United States Patent [19]

Letelier et al.

[11] 4,014,921
[45] Mar. 29, 1977

[54] O-ACETOXY BENZOATE ESTER OF 2(p-ACETAMIDO-PHENYLOXY)ETHYL ALCOHOL

[75] Inventors: Carlos Sunkel Letelier; Fernando Cillero Grafulia, both of Madrid, Spain

[73] Assignee: Alter, S.A., Spain

[22] Filed: Aug. 15, 1975

[21] Appl. No.: 605,090

[30] Foreign Application Priority Data

July 11, 1975 Spain ................................. 439340

[52] U.S. Cl. .......................... 260/473 R; 424/309
[51] Int. Cl.$^2$ ....................................... C07C 69/66
[58] Field of Search ............................. 260/473 R

[56] References Cited
OTHER PUBLICATIONS

March, J., Advanced Organic Chemistry: Reactions, Mechanisms, & Structure; Mcgraw-Hill Book Co. June 11, 1968; p. 319.

Primary Examiner—Paul J. Killos
Attorney, Agent, or Firm—Ladas, Parry, Von Gehr, Goldsmith & Deschamps

[57] ABSTRACT

The o-acetoxy benzoate ester of 2(p-acetamido-phenyloxy)-ethyl alcohol.

1 Claim, No Drawings

O-ACETOXY BENZOATE ESTER OF 2(p-ACETAMIDO-PHENYLOXY)ETHYL ALCOHOL

The present invention relates to the o-acetoxy benzoate ester of 2(p-acetamido-phenyloxy)-ethyl alcohol. This ester is of formula (I).

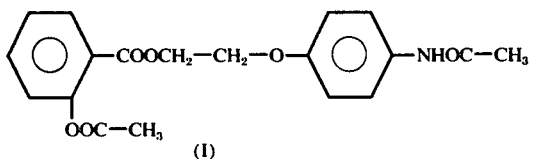

(I)

This compound presents interesting therapeutic uses such as an anti-inflammatory, analgesic and antipyretic.

Thus, according to the method of Winter, C. A., Risley, E. A., and Nuss, G. W. - G. Pharmacol, 141, 369 (1963), in doses of 200 and 400 mg/Kg, this product causes edema inhibition of 23% and 31%, respectively, in such manner demonstrating its anti-inflammatory activity.

The analgesic activity is demonstrated by means of the test by Randall, L. O. and Salitto, J. J., Arch. Int. Pharmacodyn 151, 409 (1957). Doses of 200, 300 and 500 mg/Kg. cause 1.43: 1.77 and 2.09 effects over controls.

Antithermic activity was determined in rabbits, adjusting an endovenous dose of yeast extract to achieve a + 1.7° C rise over the basal temperature of the animal. Three hours after injecting the pyrogenic agent, 200 mg/Kg of the product were administered interperitoneally. For two consecutive hours the animal's temperature decreased to its basal values.

TOXICITY TESTS.

As it has been possible to demonstrate experimentally, Product (I) is less toxic than aspirin. The test carried out by oral administration in a rat reflects an $LD_{50}$ of 978 mg/Kg. for aspirin, and the maximum dose of the compound it has been possible to administer has 7,000 mg/Kg., which corresponds to its $LD_{10}$. One only dose of 500 mg/Kg of compound (I) to aspirin in 2 10-rat groups resulted in no ulcers either of the stomach or intestine, although the stomachs of 60% of the rats treated with aspirin revealed hemorrhagic content.

ADVANTAGES OF THE PRODUCT a. As an anti-inflammatory it is as active as aspirin and 33 times less active than indometacine. Despite this difference, the anti-inflammatory $ED_{50}$ of product (I) is 10 times lower than the $LD_{50}$ of same, while the anti-inflammatory $ED_{50}$ of indometacine is very close to the toxic range of the product.

b. As an analgesic it is equipotential with respect to aspirin; if factor 7 toxicity is taken into account, the former can be considered advantageously.

c. As an antipyretic it is similar to aspirin and to N-acetyl-p-aminophenol insofar as antithermic power, although it offers the advantage of longer lasting effects.

d. As regards gastrointestinal disorders, in an acute test with 500 mg/Kg., clear differences appear in favor of compound (I) over aspirin.

Obtention of this compound is effected by causing a reaction of p-acetamidophenol-β-oxyethyl ether of formula (II).

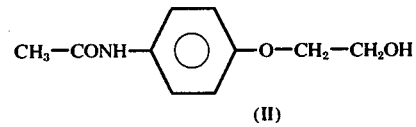

(II)

with o-Acetoxibenzoic acid chloride within an inert solvent — chloroform, for example — and in the presence of a base such as triethylamine. Compound (I) can be obtained in this manner, yield being 70%.

It is understood that neither the solvent employed nor the base are of a nature other than that which is merely illustrative.

A possible form for batching the compound (I) can be represented by the following formula per tablet:

| | |
|---|---|
| o-Acetoxybenzoate from 2-(p-acetamidophenyloxy)ethyl | 500 mg. |
| Talcum | 3 mg. |
| Calcic stearate | 2 mg. |
| Lactose | 65 mg. |
| Starch | 30 mg. |

EXAMPLE

OBTENTION OF O-ACETOXYBENZOATE FROM 2-(P-ACETAMIDOPHENYLOXY)ETHYL

To a solution of 199 grs. o-Acetoxybenzoic acid chloride in 1,000 ml. chloroform are added 195 grs. p-acetamidophenol-β-oxyethyl ether and 140 ml. triethylamine. The mixture is stirred for 6 hours at room temperature. Such time having elapsed, the solution is washed with water three times; it is dried in anhydrid sodium sulphate and the solvent is evaporated. Once methanol recrystallized, the solid residue melts at 139°–141° C. Reagent yield is 70% (252 grs.).

Analysis estimated for $C_{19}H_{19}NO_6$: C, 63.86%; H, 5,36 %; N, 3.92%. Found: C, 63.78%; H, 5.29%, N, 4.10%.

We claim:

1. O-acetoxy benzoate ester of 2(p-acetamidophenyloxy)-ethyl alcohol of the formula

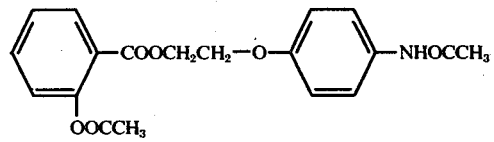

* * * * *